(12) United States Patent
Muddasani et al.

(10) Patent No.: US 9,227,948 B2
(45) Date of Patent: Jan. 5, 2016

(54) PROCESS FOR THE PREPARATION OF 2-SUBSTITUTED-2-(6-(SUBSTITUTED)-7-METHYLBENZO[D][1,3]DIOXOL-4-YL) ACETIC ACID DERIVATIVES

(71) Applicant: Natco Pharma Limited, Banjara Hills (IN)

(72) Inventors: Pulla Reddy Muddasani, Banjara Hills (IN); Manikumar Chintalapudi, Banjara Hills (IN); Venkaiah Chowdary Nannapaneni, Banjara Hills (IN)

(73) Assignee: Natco Pharma Limited, Banjara Hills, Hyderabad (IN)

( * ) Notice: Subject to any disclaimer, the term of this patent is extended or adjusted under 35 U.S.C. 154(b) by 0 days.

(21) Appl. No.: 14/408,534

(22) PCT Filed: Jun. 19, 2013

(86) PCT No.: PCT/IN2013/000381
§ 371 (c)(1),
(2) Date: Dec. 16, 2014

(87) PCT Pub. No.: WO2013/190571
PCT Pub. Date: Dec. 27, 2013

(65) Prior Publication Data
US 2015/0119587 A1    Apr. 30, 2015

(30) Foreign Application Priority Data

Jun. 19, 2012 (IN) .......................... 2429/CHE/2012

(51) Int. Cl.
| | |
|---|---|
| C07D 309/12 | (2006.01) |
| C07D 317/64 | (2006.01) |
| C07F 7/18 | (2006.01) |
| C07C 43/23 | (2006.01) |
| C07C 59/64 | (2006.01) |
| C07C 69/734 | (2006.01) |

(52) U.S. Cl.
CPC .............. C07D 317/64 (2013.01); C07C 43/23 (2013.01); C07C 59/64 (2013.01); C07C 69/734 (2013.01); C07D 309/12 (2013.01); C07F 7/1856 (2013.01)

(58) Field of Classification Search
CPC .. C07D 309/12; C07D 317/64; C07F 7/1856; C07C 43/23; C07C 59/64; C07C 69/734
See application file for complete search history.

(56) References Cited

U.S. PATENT DOCUMENTS 4,435,601 A    3/1984 Formanek et al.

OTHER PUBLICATIONS

Chen, et al., Total Synthesis of Ecteinascidin 743, J. Am. Chem. Soc., 35, 128, 87-89, (2006).*

(Continued)

*Primary Examiner* — Erich A Leeser
(74) *Attorney, Agent, or Firm* — Kilpatrick Townsend & Stockton LLP

(57) ABSTRACT

Present invention relates to an improved and commercial process for the preparation of 2-sustituted-2-(6-(substituted)-7-methylbenzo[d][1,3]dioxol-4-yl)acetic acid derivatives of formula-I the above Formula I, XII, XIII, XV, wherein $R_1$ is a O-protecting group such as methoxymethyl, ethoxymethyl, trialkylsilyl, arylmethyl, tetrahydropyran-2-yl, allyl; X is hydroxyl, halogen, mesylate, triflate, tosylate, acetate; Y is oxygen atom, NH or sulfur atom; $R_2$ is $C_1$-$C_6$ alkyl. 2,4-Dihydroxy-3-methylbenzaldehyde is selectively protected at C-4 position in the form of an ether compound of formula-XII, oxidized the aldehyde function to get the diol of formula-XIII, and condensed with ethyl glyoxalate under Casiraghi reaction conditions to get the compound of formula-XV. Compound of formula-XV is converted to compound of formula-I by conventional chemistry. Compounds of formula-I are key intermediates in the synthesis of ecteinascidines like trabectedin.

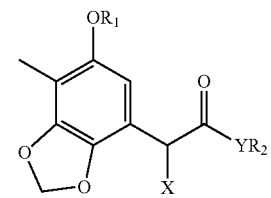

I

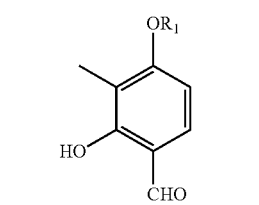

XII

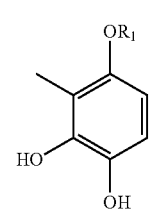

XIII

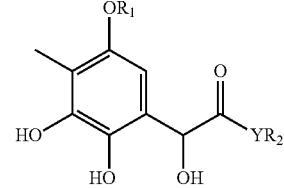

XV

27 Claims, No Drawings

(56) References Cited

OTHER PUBLICATIONS

Casiraghi et al., "Synthesis of 1-(2-Hydroxyaryl)-1,2,3-propanetriol and 1-(2- Hydroxyaryl)-2-amino-1,3-propanediol Derivatives of either *threo* or *erythro* Configuration," J. Org. Chem., 1988, vol. 53, pp. 4919-4922.

Chen et al., "Total Synthesis of Ecteinascidin 743," J. Am. Chem. Soc., 2006, vol. 128, pp. 87-89.

Mendelson et al., "The Regioselective 4-Benzylation of 2,4-Dihydroxybenzaldehyde," Synthetic Communications, 1996, vol. 26(3), pp. 593-601.

Nicolaou et al., "Total Synthesis of Sporolide B and 9-*epi*-Sporolide B," J. Am. Chem. Soc., 2010, vol. 132, pp. 11350-11363.

Nielsen et al., "Antileishmanial Chalcones: Statistical Design, Synthesis, and Three-Dimensional Quantitative Structure-Activity Relationship Analysis," J. Med. Chem., 1998, vol. 41, pp. 4819-4832.

Volp et al., "A Concise Synthetic Approach to the Sorbicillactones: Total Synthesis of Sorbicillactone A and 9-*epi*-Sorbicillactone A," Organic Letters, 2011, vol. 13(17), pp. 4486-4489.

Zhou et al., "Studies Directed to the Total Synthesis of ET 743 and Analogues Thereof: An Expeditious Route to the ABFGH Subunit," Organic Letters, 2002, vol. 4(1), pp. 43-46.

International Search Report, Oct. 7, 2013, PCT application No. PCT/IN2013/000381, 2 pages.

\* cited by examiner

PROCESS FOR THE PREPARATION OF 2-SUBSTITUTED-2-(6-(SUBSTITUTED)-7-METHYLBENZO[D][1,3]DIOXOL-4-YL) ACETIC ACID DERIVATIVES

FIELD OF INVENTION

Present invention relates to an improved and commercial process for the preparation of 2-sustituted-2-(6-(substituted)-7-methylbenzo[d][1,3]dioxol-4-yl)acetic acid derivatives of formula-I

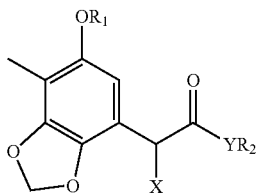

Wherein $R_1$ is a O-protecting group such as methoxymethyl, ethoxymethyl, trialkylsilyl, arylmethyl, tetrahydropyran-2-yl, allyl; X is hydroxyl, halogen, mesylate, triflate, tosylate, acetate; Y is oxygen atom, NH or sulfur atom; $R_2$ is $C_1$-$C_6$ alkyl Compounds of formula-I are key intermediates useful in the synthesis of Ecteinascidins such as Ecteinascidin 743, Ecteinascidin 736, Ecteinascidin 729, Ecteinascidin 722, Ecteinascidin 637, and Ecteinascidin 594. Ecteinascidins are a family of tetrahydroisoquinoline alkaloids isolated from the Caribbean tunicate *Ecteinascidia turbinate*, which possess potent cytotoxic acitivity against a variety of turners. One of its members, Ecteinascidin 743 (Et 743, commercial name Yondelis) is approved in the United States for ovarian, endometrium, and breast cancer. Yondelis has been granted Orphan Drug Designation by the US FDA and Europian Commission for the treatment of cancer. The antiproliferative activity of Et 743. is greater than that of taxol, camptothecin, adriamycin, mitomycin C, cisplatin, and etoposide by 1-3 fold orders of magnitude.

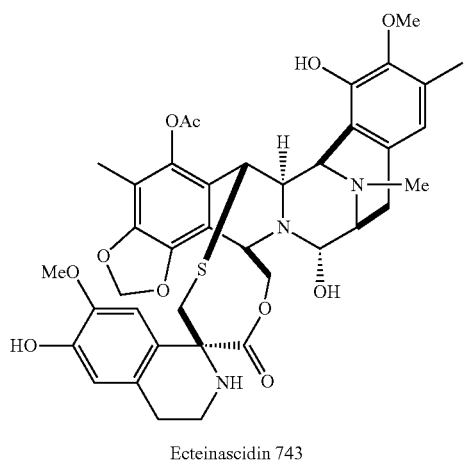

Ecteinascidin 743

BACKGROUND OF INVENTION

Compound of formula-I wherein $R_1$ is methoxymethyl (MOM), $R_2$ is ethyl, Y is oxygen atom and X is hydroxyl or bromo is used by Jieping Zhu, et al in their synthesis of Ecteinascidin 743 (J. Am. Chem. Soc., 2006, 128, pages 87-89). According to the process given in this reference, sesamol is protected with methoxymethyl group and converted to compound of formula-III by reacting with n-butyl lithium and trimethyl borate (Scheme-I). Compound of formula-III is reacted with ethyl glyoxalate in the presence of hexafluoroisopropanol to get the compound of formula-IV. Triflation of compound of formula-IV followed by reaction with trimethylboroxine in the presence of palladium (tetrakistriphenylphosphine) gave the compound of formula-VI. Reaction of compound of formula-VI with thionyl bromide gave the compound of formula-VII. Compound of formula-VII is used as a key intermediate in the synthesis of Ecteinascidin 743.

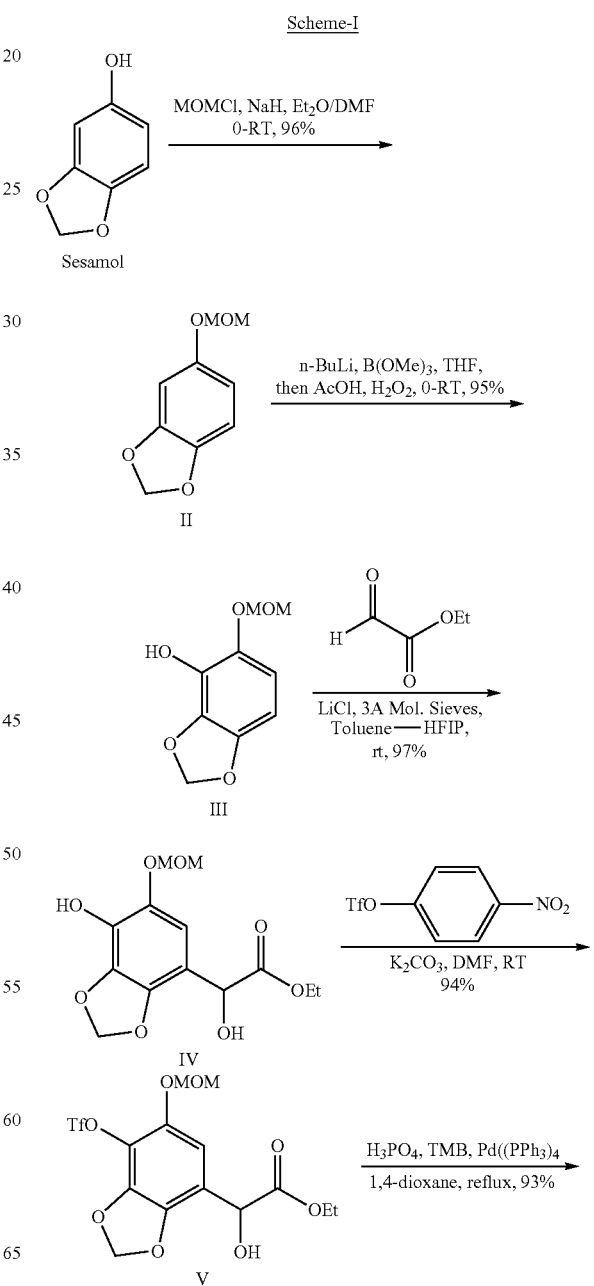

Scheme-I

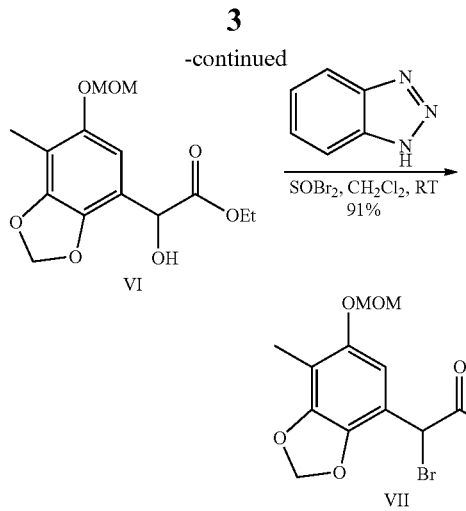

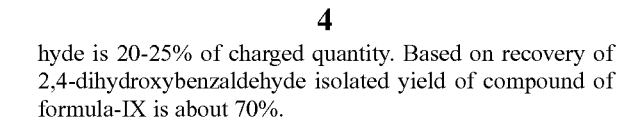

Main drawback in this process is the handling of costly, toxic, and pyrophoric reagents. Another main drawback in the synthesis is the non-availability of trimethylboroxine on commercial scale.

Keeping in view of the difficulties in commercialization of the above-mentioned process for the preparation of compound of formula-I, we aimed to develop a simple, economical, and commercial process.

We observed that a promising approach for a process for the preparation of compound of formula-I would be to (a) avoid the usage of costly and difficult to handle reagents.

Accordingly, the main objective of the present invention is to provide an improved process for the preparation of compound of formula-I, which is commercially applicable.

PROCESS OF THE PRESENT INVENTION

The present invention has been developed based on our finding that 3-methyl-2,4-dihydroxybenzaldehyde would be a suitable starting material for the synthesis of compound of formula-I than the sesamol (Scheme-II). Hydroxy group present at 4-position in 3-methyl-2,4-dihydroxybenzaldehyde is known to undergo selective etherification (Org. Lett. 2011, 13(17), 4486-89; J. Med. Chem., 1998, 41, 4819-4832; Synthetic Commun. 1996, 26(3), 593-601). Therefore, compound of formula-VIII is reacted with methoxymethyl chloride in the presence of a base to get the compound of formula-IX. During process optimization studies it was observed that along with the required compound of formula-IX (about 75% by GC) about 3% of 4-hydroxy-2-methoxymethoxy-3-methylbenzaldehyde and 20% of 2,4-bis(methoxymethoxy)-3-methylbenzaldehyde were formed. Fortunately, crystallization of crude from a polar solvent like isopropanol removed all the impurities and the purity of required product (compound of formula-IX) was found to be more than 98% by GC. Isolated yield of compound of formula-IX is 55-60%. Alternatively, crude compound of formula-IX was also purified to more than 95% by high vacuum distillation. Compound of formula-IX distilled at 140-150° C. (bath temperature) at a vacuum of 1.0 mmHg. Distilled compound of formula-IX contained 2-3% of 2,4-bis(dimethoxymethoxy)-3-methylbenzaldehyde. Mother liquors of crystallization were collected, distilled of IPA partially and treated with 1N HCl at room temperature to form 2,4-dihydroxybenzaldehyde. The formed 2,4-dihydroxybenzaldehyde was collected by filtration of reaction mass. Recovery of 2,4-dihydroxybenzaldehyde is 20-25% of charged quantity. Based on recovery of 2,4-dihydroxybenzaldehyde isolated yield of compound of formula-IX is about 70%.

Scheme-II

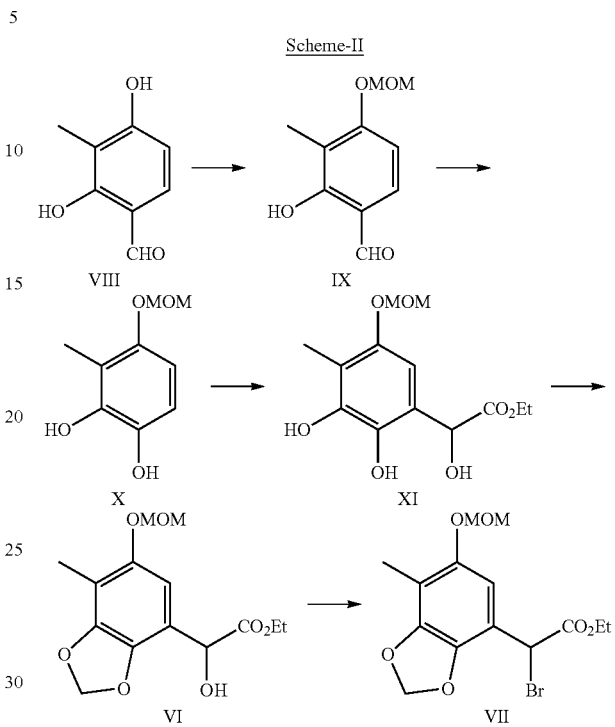

Compound of formula-IX is oxidized under Dakin oxidation conditions (U.S. Pat. No. 4,435,601) in basic medium to get the compound of formula-X. Dihydroxy compound of formula-X is condensed with ethyl glyoxalate under Casiraghi (Casiraghi, G.; Cornia, M.; Rassu, G. *J. Org. Chem.* 1988, 53, 4919-4922) conditions to get the compound of formula-XI. Surprisingly, no regio-isomeric condensation product was formed in this reaction. Compound of formula-XI is reacted with dihalomethane such as bromochloromethane in the presence of a base to get the compound of formula-VI. Compound of formula-VI is converted to compound of formula-VII under prior art conditions or by other brominating agents.

Accordingly, process of the present invention provides an improved process for the preparation of compound of formula-I,

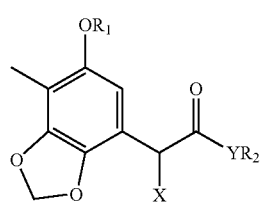

Wherein $R_1$ is a O-protecting group such as methoxymethyl, ethoxymethyl, trialkylsilyl, arylmethyl, tetrahydropyran2-yl, allyl; X is hydroxyl, halogen, mesylate, tosylate, triflate, acetate; Y is oxygen atom, NH or sulfur atom; $R_2$ is $C_1$-$C_6$ alkyl which comprises:

(i) Reaction of 2,4-dihydroxy-3-methylbenzaldehyde with an etherification reagent in the presence of a base (or acid in case of tetrahydropyran-2-yl protection) to get the mono-protected derivative of formula-XII,

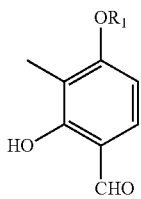

XII

Wherein $R_1$=methoxymethyl, ethoxymethyl, trialkylsilyl, tetrahydropyran-2-yl, allyl, arylmethyl (ii) Oxidation of compound of formula-XII with an oxidizing agent in the presence of a base to get the dihydroxy compound of formula-XIII,

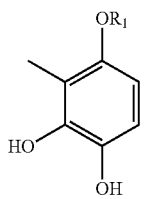

XIII

Wherein $R_1$=methoxymethyl, ethoxymethyl, trialkylsilyl, arylmethyl, tetrahydropyran-2-yl, allyl;

(iii) Reaction of dihydroxy compound of formula-XIII with a base and an aldehyde compound of formula-XIV,

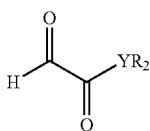

XIV

Wherein Y and $R_2$ are as defined above
to get the compound of formula-XV,

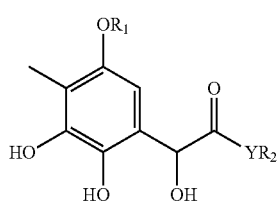

XV

Wherein $R_1$, Y, and $R_2$ are as defined above (iv) Reaction of dihydroxy compound of formula-XV with a dihalomethane in the presence of a base to get the methylenedioxy derivative of formula-XVI

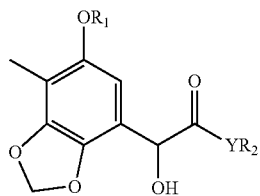

XVI

Wherein $R_1$, Y, and $R_2$ are as defined above.

(v) Conversion of hydroxyl group to X wherein X is as defined above using a suitable reagent to get the compound of formula-I

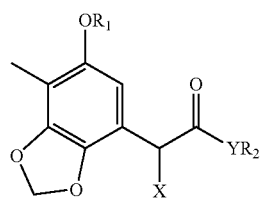

I

Wherein $R_1$, $R_2$, X, and Y are as defined above

In a preferred embodiment of the present invention in step (i) 2,4-dihydroxy-3-methylbenzaldehyde is reacted with etherification reagents such as alkoxymethyl halides like methoxymethyl chloride, ethoxymethylchloride; silyl halides such as trimethylsilyl chloride, triethylsilyl chloride, tert-butyldimethylsilyl chloride, tert-butyldiphenylsilyl chloride, allyl halide, aryl halide, etc., in the presence of a base such as trialkylamine, sodium or potassium carbonate, bicarbonate, etc. in an organic solvent such as halogenated solvents, ethers, hydrocarbons to get the mono-protected compound of formula-XII. In the case of tetrahydropyran-2-yl derivative an acid catalyst like, p-toluenesulfonic acid is preferred over a base. Temperature of the reaction can be 10° C. to the boiling point of the solvent employed in the reaction, preferably 25-30° C.

In step (ii) oxidizing reagent employed in the reaction is hydrogen peroxide, per acids like m-chloroperbenzoic acid, peracetic acid, or any other equivalent. Base employed in step (ii) is selected from sodium or potassium bicarbonate, carbonate, hydroxide, preferably sodium or potassium hydroxide. In step (iii) base employed in the reaction is C1-C6alkylmagnesium chloride or bromide. Solvent employed in the reaction is a halogenated solvent, ether solvent, hydrocarbon solvent, etc. or a mixture thereof, preferably a mixture of hydrocarbon and ether solvent.

In step (iv) dihalomethane reagent employed in the reaction is bromochloromethane, bromoiodomethane, dibromomethane, dichloromethane, diiodomethane, preferably bromochlororethane. Base employed in the reaction is a carbonate or bicarbonate of sodium, potassium cesium, etc., preferably cesium carbonate. Solvent employed in the reaction is a dipolar aprotic solvent such as dimethylformamide or a polar solvent such as acetonitrile and the temperature of the reaction is 25-120° C.

In step (v) reagents employed for suitable X are thionyl chloride, methanesulfonyl chloride, triflic anhydride, acetyl chloride, acetic anhydride, p-toluenesulfonyl chloride, etc. Additionally, a base such as benzotriazole, diazabicycloundecane, DCC, DBU, etc., may be used do the required conversion. When X is a halide preferred reagents are a combination of carbon tetrahalide with triphenylphosphine and catalytic amount of a base like diisopropylethylamine.

Advantages of Present Invention

1. Present process uses all cheap and readily available raw materials.
2. Present process avoids the usage of toxic and costly reagents such as sodium hydride, n-butyl lithium, trimethylboroxine, tetrakis(triphenylphosphine)palladium (0), p-nitro-phenyltrifluoromethanesulfonate, 1,1,1,3,3,3-hexafluoroisopropanol, thionyl bromide, etc.
3. Present process is short, simple, and free from usage of hazardous reagents.
4. Present process is economically and commercially viable.

The details of the invention are given in the Examples given below which are provided to illustrate the invention only and therefore should not be construed to limit the scope of the present invention.

EXAMPLES

Example 1

Preparation of 2,4-dihydroxy-3-methylbenzaldehyde

Into a clean and dry 2 L, 4-Necked RB Flask, charged 600 ml of dichloromethane under nitrogen atmosphere at RT. N,N-Dimethylformamide (324 g) was charged to the reaction mass under stirring at RT. Reaction mass was cooled to 0-5° C. Phosphorous oxychloride (568 g) was slowly added to the reaction mass at 0-5° C. After completion of the addition, mass was allowed to reach 25° C. and maintained at 25-30° C. for 1.5 h. The reaction mass was cooled 0-5° C. 2-Methylresorcinol (200 g) was added in lots maintaining the mass temperature at 0-5° C. Reaction mass was maintained for 16 h at RT, poured into chilled water (2500 ml). Reaction mass was stirred for 15 h at 25-30° C. and filtered under suction. The wet cake was washed with 1000 ml water and dried under vacuum at 60-65° C. for 6 h to get 210 g of title compound as an off-white solid.

Example 2

(i) Preparation of 2-hydroxy-4-(methoxymethoxy)-3-methylbenzaldehyde

Into a clean and dry 5 L, 4-Necked RB Flask was charged 2000 ml of dichloromethane under nitrogen atmosphere at RT. 2,4-Dihydroxy-3-methylbenzaldehyde (200 g) was added to the reaction mass under stirring at RT. N,N-Diisopropylethylamine (290 g) was slowly added to the reaction mass under stirring at RT. The reaction mass was cooled to 0-5° C. Methoxymethyl chloride (prepared from 159.5 g of dimethoxymethane, 164.5 g of acetyl chloride and 12 mg of zinc bromide) was added to the reaction mass at 0-5° C. The reaction mass was allowed to RT and maintained for 15 h under stirring. Aqueous ammonium chloride (200 ml) was added to the reaction mass under stirring and kept under stirring for 0.5 h. Organic layer was separated and washed with 600 ml of saturated sodium bicarbonate solution. Organic layer was dried with $Na_2SO_4$ and distilled of solvent. The residue (232 g containing 17% of 2,4-bis(methoxymethoxy)-3-methylbenzaldehyde by GC) was treated with 300 ml of IPA at 40-45° C., cooled to RT, further cooled to 0-5° C. and maintained for 3 h. The reaction mass filtered under suction and washed the wet cake with 120 ml of chilled (0-5° C.) IPA. The wet material was dried under vacuum at 40° C. for 5 h to get 150 g of title compound as off-white solid. Purity of title compound by GC is 97%. M.R.: 55.5-57.5° C. IR (Mk): 3289, 3099, 3009, 3003, 2917, 2829, 2743, 1644, 1590, 1495, 1448, 1389, 1308, 1284, 1249, 1208, 1160, 1106, 1071, 1020, 974, 922, 879, 810, 745, 689, 638, and 608 cm$^{-1}$. $^1$H-NMR (CDCl$_3$, 400 MHz): δ 11.39 (s, 1H, exchangeable with D$_2$O, OH), 9.48 (s, 1H, CHO), 7.60 (d, J=8.8 Hz, 1H, Ar. H), 6.82 (d, J=8.8 Hz, 1H, Ar. H), 5.34 (s, 2H, OCH$_2$O), 3.40 (s, 3H, OCH$_3$), 2.05 (s, 3H, ArCH$_3$). $^{13}$C-NMR (CDCl$_3$, 100 MHz): δ 195.81 (CHO), 161.32 (C-4), 160.13 (C-2), 132.93 (C-6), 115.73 (C-1), 112.98 (C-3), 106.06 (C-5), 93.85 (OCH$_2$O), 55.95 (OMe), 7.47 (ArCH$_3$). Mass (EI-MS): 195.4 (M–1).

2,4-bis(methoxymethoxy)-3-methylbenzaldehyde

DSC: 32.95° C. (peak). IR (KBr): 2992, 2961, 2944, 2915, 2879, 2833, 1681, 1549, 1482, 1452, 1432, 1404, 1385, 1374, 1313, 1259, 1224, 1205, 1156, 1107, 1053, 1003, 971, 928, 859, 804, 779, 761, 696, and 663 cm$^{-1}$. $^1$H-NMR (CDCl$_3$, 400 MHz): δ 10.20 (s, 1H, CHO), 7.70 (d, J=8.8 Hz, 1H, H-6), 6.98 (d, J=8.8 Hz, 1H, H-5), 5.27 (s, 2H, OCH$_2$O), 5.08 (s, 2H, OCH$_2$O), 3.61 (s, 3H, OMe), 3.49 (s, 3H, OMe), 2.21 (s, 3H, ArCH$_3$). $^{13}$C-NMR (CDCl$_3$, 100 MHz): δ 189.47 (CHO), 161.27 (C-4), 159.75 (C-2), 127.88 (C-6), 123.97 (C-1), 120.95 (C-3), 109.82 (C-5), 100.92 (OCH$_2$O of C-2), 94.16, (OCH$_2$O of C-4), 57.76 (OCH$_3$), 56.20 (OCH$_3$), 9.34 (ArCH$_3$).

Recovery of 2,4-Dihydroxy-3-methylbenzaldehyde

IPA MLs were collected and distilled of IPA under vacuum at 60° C. to keep about one volume of IPA to the weight of residual mass. The residue was cooled and treated with 750 ml of 1N HCl. Reaction mass was stirred for 48 hours at RT and filtered. The wet cake was washed with water, toluene and dried at 60° C. under vacuum to get 45 g of 2,4-dihydroxy-3-methylbenzaldehyde.

Example 3

Preparation of 4-(ethoxymethoxy)-2-hydroxy-3-methylbenzaldehyde

By following Example 2 procedure, 25.0 g of 2,4-dihydroxy-3-methylbenzaldehyde was reacted with 40.0 g of ethoxymethyl chloride (prepared from 23 g of diethoxymethane and 17.3 g of acetyl chloride) and 31.8 g of N,N-diisopropylethylamine to get 36.0 g of crude title product containing 11.5% of 2,4-bis(ethoxymethoxy)-3-methylbenzaldehyde by GC. Crude product was purified by column chromatography to get the title compound (25.0 g) as white solid. DSC: 43.1° C. (peak). IR (KBr): 3283, 3095, 3038, 2972, 2952, 2909, 2876, 2807, 2765, 2734, 1641, 1621, 1584, 1492, 1453, 1434, 1396, 1320, 1298, 1242, 1176, 1128, 1094, 1071, 1017, 978, 882, 849, 807, 777, 736, 691, 642, and 617 cm$^{-1}$. $^1$H-NMR (CDCl$_3$, 400 MHz): δ 11.48 (s, 1H, exch. with D$_2$O, OH), 9.73 (s, 1H, CHO), 7.35 (d, J=8.8 Hz, 1H, H-6), 6.78 (d, J=8.8 Hz, 1H, H-5), 5.33 (s, 2H, OCH$_2$O), 3.74 (q, J=6.8 Hz, 2H, OC$\underline{H}_2$CH$_3$), 2.12 (s, 3H, ArCH$_3$), 1.23 (t, J=6.8 Hz, 3H, OCH$_2$C$\underline{H}_3$) $^{13}$C NMR (CDCl$_3$, 100 MHz): δ 194.91 (CHO), 162.11 (C-4), 161.30 (C-2), 132.72 (C-6), 115.72 (C-1), 114.26 (C-3), 105.82 (C-5), 92.81 (OCH$_2$O), 64.76 (OCH$_2$CH$_3$), 15.06 (OCH$_2$CH$_3$), 7.47 (ArCH$_3$). Mass (EIMS): 210.17 (M), 209.10 (M−1).

2,4-bis(ethoxymethoxy)-3-methylbenzaldehyde

IR (liquid, neat): 2978, 2931, 2892, 1680, 1593, 1483, 1444, 1385, 1308, 1254, 1233, 1211, 1155, 1117, 1094, 1053, 1020, 992, 943, 859, 815, 779, and 674 cm$^{-1}$. $^1$H-NMR (CDCl$_3$, 400 MHz): δ 0.19 (s, 1H, CHO), 7.71 (d, J=8.8 Hz, 1H, H-6), 7.00 (d, J=8.8 Hz, 1H, H-5), 5.32 (s, 2H, OCH$_2$O), 5.12 (s, 2H, OCH$_2$O), 3.84 (q, J=7.2 Hz, 2H, OCH$_2$CH$_3$), 3.74 (q, J=7.2 Hz, 2H, OCH$_2$CH$_3$), 2.19 (s, 3H, ArCH$_3$), 1.25 (t, J=7.2 Hz, 3H, OCH$_2$CH$_3$), 1.23 (t, J=7.2 Hz, 3H, OCH$_2$CH$_3$). $^{13}$C-NMR (CDCl$_3$, 100 MHz): δ 189.69 (CHO), 161.53 (C-4), 159.81 (C-2), 127.82 (C-6), 123.99 (C-1), 120.86 (C-3), 109.40 (C-5), 99.40 (OCH$_2$O), 92.93 (OCH$_2$O), 66.04 (OCH$_2$), 64.69 (OCH$_2$), 15.00 (2×OCH$_2$CH$_3$), 9.42 (ArCH$_3$). Mass (EI-MS): 241.1 (M+1).

Example 4

Preparation of 4-(tert-butyldimethylsilyloxy)-2-hydroxy-3-methylbenzaldehyde

By following Example 2 procedure, 5.0 g of 2,4-Dihydroxy-3-methylbenzaldehyde was reacted with 4.95 g of tert-butyldimethylsilyl chloride and 2.15 g of N,N-diisopropylethylamine to get 7.91 g of crude title product containing 16.5% of 2,4-bis(tert-butyldimethylsilyloxy)-3-methylbenzaldehyde by GC. Crude product was purified by column chromatography to get the title compound as colorless liquid. IR (neat): 3280, 2956, 2932, 2888, 2859, 1646, 1622, 1582, 1493, 1425, 1388, 1360, 1325, 1296, 1249, 1171, 1103, 1021, 1007, 846, 798, 726, 679, 652, and 610 cm$^{-1}$. $^1$H-NMR (CDCl$_3$, 400 MHz): δ 11.56 (s, 1H, exch. with D$_2$O, OH), 9.70 (s, 1H, CHO), 7.26 (d, J=8.4 MHz, 1H, aromatic H-6), 6.45 (d, J=8.4 Hz, 1H, aromatic H-5), 2.10 (s, 3H, ArCH$_3$), 1.02 (s, 9H, Si-tert-Bu), 0.27 (s, 6H, SiMe$_2$). $^{13}$C NMR (CDCl$_3$, 100 MHz): δ 194.73 (CHO), 162.12 (C-2), 161.44 (C-4), 132.26 (C-6), 116.45 (C-1), 115.39 (C-3), 111.26 (C-5), 25.26 (CMe$_3$), 18.29 (CMe$_3$), 8.15 (ArCH$_3$), 8.19 (SiMe$_2$). Mass (EIMS): 266.26 (M), 265.19 (M−1).

Example 5

Preparation of 4-allyloxy-2-hydroxy-3-methylbenzaldehyde

By following Example 2 procedure, 5.0 g of 2,4-dihydroxy-3-methylbenzaldehyde was reacted with 8.35 g of allyl chloride and 5.1 g of N,N-diisopropylethylamine to get 8.41 g of crude title product containing 12% of 2,4-bis(allyloxy)-3-methylbenzaldehyde by GC. Crude product was purified by column chromatography to get the title compound as liquid. IR (neat): 3280, 3088, 3024, 2988, 2926, 2838, 2748, 1645, 1585, 1499, 1452, 1427, 1388, 1353, 1330, 1290, 1250, 1182, 1110, 1022, 990, 928, 891, 788, 758, 715, and 646 cm$^{-1}$. $^1$H-NMR (CDCl$_3$, 400 MHz): δ 11.45 (s, 1H, exch. with D$_2$O, OH), 9.70 (s, 1H, CHO), 7.34 (d, J=8.8 Hz, 1H, H-6), 6.53 (d, J=8.8 Hz, 1H, H-5), 6.06 (m, 1H, CH=CH$_2$), 5.44 (dq, J=1.6, 19.2 Hz, 1H, CH=CH$_2$), 5.32 (dq, J=1.2, 10.8 Hz, 1H, CH=CH$_2$), 4.64 (dt, J=1.6, 4.8 Hz, 2H, CH$_2$=CHCH$_2$), 2.13 (s, 3H, ArCH$_3$). $^{13}$C NMR (CDCl$_3$, 100 MHz): δ 194.60 (CHO), 163.17 (C-4), 160.99 (C-2), 133.00 (CH$_2$=CH); 132.38 (C-5), 117.55 (CH$_2$=CH), 113.48 (C-1), 103.75 (C-5), 68.90 (OCH$_2$), 7.30 (ArCH$_3$). Mass (EI-MS): 192.1 (M), 191.3 (M−1).

Example 6

Preparation of 2-hydroxy-3-methyl-4-(tetrahydro-2H-pyran-2-yloxy)benzaldehyde

By following Example 2 procedure, 10.0 g of 2,4-Dihydroxy-3-methylbenzaldehyde was reacted with 48.3 g of 3,4-dihydro-2H-pyran in the presence of 1.6 g of pyridinium para-toluenesulfonate to get 15.0 g of crude title product. Formation of 3-methyl-2,4-bis(tetrahydro-2H-pyran-2-yloxy)benzaldehyde was not noticed either by GC or TLC of the crude sample. Crude product was purified by column chromatography to get the title compound as white solid. DSC: 58.2° C. (peak). IR (KBr): 3125, 2946, 2870, 2747, 1645, 1623, 1585, 1494, 1431, 1388, 1356, 1327, 1288, 1246, 1204, 1181, 1121, 1091, 1036, 1022, 955, 921, 895, 872, 799, 758, 712, and 642 cm$^{-1}$. $^1$H-NMR (CDCl$_3$, 400 MHz): δ 11.49 (s, 1H, exch. with D$_2$O, OH), 9.72 (s, 1H, CHO), 7.33 (d, J=8.8 Hz, 1H, H-6), 6.78 (d, J=8.8 Hz, 1H, H-5), 5.58 (t, J=2.8 Hz, 1H, OCHO), 3.81 (dt, J=2.8 Hz, 11.2 Hz, 1H, CH$_2$O), 3.61-3.66 (m, 1H, CH$_2$O), 2.15 (s, 3H, ArCH$_3$), 2.00-2.05 (m, 1H, CH$_2$CHO), 1.89-1.93 (m, 2H, CH$_2$CHO and CH$_2$CH$_2$CHO), 1.62-1.75 (m, 3H, OCH$_2$CH$_2$CH$_2$). $^{13}$C NMR (CDCl$_3$, 100 MHz): δ 194.80 (CHO), 161.62 (C-4), 161.20 (C-2), 132.71 (C-6), 115.47 (C-1), 114.05 (C-3), 106.17 (C-5), 95.67 (OCHO), 61.89 (C-6'), 30.00 (C-2'), 24.97 (C-5'), 18.36 (C-4'), 7.38 (ArCH$_3$). Mass (EI-MS): 236.24 (M), 235.10 (M−1).

Example 7

Preparation of 4-(methoxymethoxy)-3-methylbenzene-1,2-diol

Into a 2.0 L, 4-Necked, RB flask equipped with two addition funnels, thermometer socket and a pH meter was charged 800 mL of DM water. The contents were kept under nitrogen atmosphere. 2-Hydroxy-4-(methoxymethoxy)-3-methylbenzaldehyde (100 g) was added to the reaction mass under stirring. Aqueous sodium hydroxide (0.5 mL, dissolve 24.6 g of sodium hydroxide in 82.0 mL of DM Water) was added to the reaction mass to get a pH of 7.0-8.0. Reaction mass was heated to 40-45° C. Simultaneous addition of aqueous sodium hydroxide and hydrogen peroxide to, the reaction was started using two addition funnels. During the addition pH of the reaction mass was maintained at 7.8-8.4 and the temperature at 40-45° C. After the completion of addition, maintained the reaction mass at 40-45° C. for 4.0 h. The reaction mass was cooled to 25-30° C. and extracted with 3×500 mL of ethyl acetate. Combined organic layer was washed with 500 mL of saturated NaCl solution, treated with 20 g of activated carbon, dried with sodium sulphate, and distilled of solvent under vacuum to get 90 g of crude 4-(methoxymethoxy)-3-methylbenzene-1,2-diol as thick syrup. HPLC purity of sample is about 85%. The material is directly used in next stage. A small sample is purified by column chromatography for characterization purpose. M.R.: 60.5-61.5° C. IR (neat): 3487, 3200, 2969, 2942, 1630, 1621, 1488, 1443, 1405, 1378, 1307, 1290, 1242, 1150, 1086, 1042, 1007, 987, 904, 881, 806, 735, 660, 606 cm$^{-1}$. $^1$H-NMR (CDCl$_3$, 400 MHz): δ 8.79 (s, 1H, exchangeable with D$_2$O, OH), 8.19 (s, 1H, exchangeable with D$_2$O, OH), 6.51 (d, J=8.4 Hz, 1H, Ar. H), 6.34 (d, J=8.8 Hz, 1H, Ar. H), 5.02 (s, 2H, OCH$_2$O), 3.36 (s, 3H, OMe), 2.01 (s, 3H, ArCH$_3$). $^{13}$C-NMR (CDCl$_3$, 100 MHz): δ 148.45 (C-4), 143.92 (C-2), 139.95 (C-1), 114.64 (C-3), 111.77 (C-6), 105.60 (C-5), 95.16 (OCH$_2$O), 55.49 (OMe), 9.17 (ArCH$_3$). Mass (EI-MS): 184.46 (M), 183.3 (M−1)

Example 8

Preparation of ethyl 2-(2,3-dihydroxy-5-(methoxymethoxy)-4-methylphenyl)-2-hydroxyacetate Into a clean and dry 3.0 L 4-necked flask, is charged 500 mL of THF and 90 g of 4-(methoxymethoxy)-3-methylbenzene-1,2-diol under N$_2$ atmosphere. The reaction mass was cooled to 20-25° C. and slowly added a solution of n-butylmagnesium chloride (560 ml, 2.0M in THF) in THF. After completion of the addition, mass temperature was raised to 40-45° C. and maintained for 90 minutes. THF was distilled under reduced pressure keeping the mass temperature 40-45° C. The reaction mass was cooled to 25-30° C. and slowly added 500 mL of toluene. The reaction mass was stirred for 15 min to get a clear solution. Ethyl glyoxalate (130 ml, 50% in toluene) was added to the reaction mixture with stirring. After completion of the addition, the reaction mixture was stirred at room temperature for 15 h. The reaction mass temperature was raised to 45-50° C. and maintained for 3 h under stirring. Reaction mass was cooled to 15-20° C. and slowly added aqueous acetic acid (100 mL of acetic acid dissolved in 1.3 L of DM Water) and stirred for 0.5 h. Reaction mass was transferred into a separating funnel and separated the top organic layer. Aqueous layer is extracted with 200 mL of toluene. The combined organic layer is washed with 2×200 mL of brine, treated with 9.0 g of activated carbon, dried with sodium sulphate, and distilled of solvent at 50-55° C. under vacuum. Isopropyl ether (150 mL) was added to the residue and heated to 50-55° C. Reaction mass was cooled to RT and maintained for 3 h, further cooled to 0-5° C. and maintained for 2 h. Reaction mass was filtered and washed the cake with 100 ml of chilled (0-5° C.) IPE. The wet solid was dried under vacuum at 50-55° C. for 6.0 h. Dry weight of title compound is 75 g. HPLC purity is 98%. M.R.: 81.0-83.0° C. IR (KBr): 3458, 3432, 2988, 2954, 2900, 2828, 1726, 1603, 1506, 1467, 1382, 1364, 1334, 1291, 1231, 1205, 1153, 1120, 1100, 1068, 1050, 994, 921, 895, 856, 834, 782, 749, 717, 677, and 622 cm$^{-1}$. $^1$H-NMR (CDCl$_3$, 400 MHz): δ 8.37 (s, 1H, exchangeable with D$_2$O, OH), 8.07 (s, 1H, exchangeable with D$_2$O, OH), 6.48 (s, 1H, Ar—H)), 5.76 (br. s, 1H, exchangeable with D$_2$O, OH), 5.29 (s, 1H, ArCHOH)), 5.02 (s, 2H, OCH$_2$O), 4.06 (q, J=7.2 Hz, OCH$_2$CH$_3$), 3.36 (s, 3H, OMe), 2.02 (s, 3H, ArCH$_3$), 1.13 (t, J=6.8 Hz, OCH$_2$CH$_3$). $^{13}$C-NMR (CDCl$_3$, 100 MHz): δ 172.78 (C=O), 148.23 (C-5), 143.99 (C-3), 138.16 (C-2), 123.93 (C-1), 114.81 (C-4), 104.99 (C-6), 95.12 (OCH$_2$O), 67.73 (ArCHOH), 60.11 (OCH$_2$CH$_3$), 55.53 OMe), 14.01 (OCH$_2$CH$_3$), 9.32 (ArCH$_3$). Mass (EI-MS): 286.64 (M), 285.47 (M−1).

Example 9

Preparation of ethyl 2-hydroxy-2-(6-(methoxymethoxy)-7-methylbenzo[d][1,3]dioxol-4-yl) acetate Into a clean and dry 2 L, 4-necked RB flask was charged 400 ml of N,N-dimethylformamide under nitrogen atmosphere at RT. Cesium carbonate (171 g) was added to the reaction mass under stirring at room temperature. Bromochloromethane (226 g) was added to the reaction mass under stirring at RT. Reaction mass was heated to 30-35° C. Ethyl 2-(2,3-dihydroxy-5-(methoxymethoxy)-4-methylphenyl)-2-hydroxyacetate (50 g) was dissolved in 100 ml of DMF and slowly added to the reaction mass under stirring at 30-35° C. Reaction mass was maintained at 30-35° C. for 2.5 h under stirring. Reaction mass was poured into 1 L toluene and stirred for 1.0 h at RT. Reaction mass was filtered through hyflow bed, and the bed washed with 600 mL of toluene. Filtrate was washed with 2.0 L of DM water. Aqueous layer was extracted with 2×500 mL of toluene. Combined organic layer was washed with 2×600 mL of saturated sodium chloride solution and treated with 7.5 g of activated carbon at 45-50° C. Reaction mass was filtered and distilled of solvent under vacuum at 45-55° C. to get 40 g of crude title compound as syrup. HPLC purity of the crude compound is 92.5%. The crude compound was directly used in next step. A small sample was purified by column chromatography to compare its spectral data with the literature values.

Example 10

Preparation of ethyl 2-bromo-2-(6-(methoxymethoxy)-7-methylbenzo[d][1,3]dioxol-4-yl) acetate Into a clean and dry 5.0 L, three-necked RB flask, is charged 163.0 g of ethyl 2-hydroxy-2-(6-(methoxymethoxy)-7-methylbenzo[d][1,3]dioxol-4-yl)acetate and 1500 mL of methylene chloride under nitrogen atmosphere. Carbon tetrabromide (218.4 g) was added to the reaction mass under stirring at 25-30° C. N,N-Diisopropylethylamine (37.8 g) was added to the reaction mass under stirring at 25-30° C. Reaction mass was cooled to −45 to −50° C. Triphenylphosphine (157.0 g, dissolved in 300 mL of methylene chloride) was added to the reaction mass under stirring at −45 to −50° C. Reaction mass was maintained for 1.5 h at −45 to −50° C. and allowed to reach 10° C. over a period of 18 h. Solvent was distilled of from the reaction mass under vacuum at 25-30° C. Ethyl acetate/hexane (1:9, 1300 ml) was added to the residue and stirred for 1.0 h. The reaction mass was filtered and the solids washed with 500 mL of (Ethyl acetate/Hexane, 1:9) solvent mixture under stirring. Filtrate was transferred into a RB flask and distilled of solvent under vacuum keeping the temperature at 25-30° C. The crude compound was purified by column chromatography to get 120 g of pure ethyl 2-bromo-2-(6-(methoxymethoxy)-7-methylbenzo[d][1,3]dioxol-4-yl)acetate as light yellow colored liquid. HPLC purity of title compound is 99.5%.

Example 11

Preparation of 4-(ethoxymethoxy)-3-methylbenzene-1,2-diol

Into a clean and dry 100 mL, 4-Necked RB Flask, charge 40 ml of Water and 5.0 g of 4-(ethoxymethoxy)-2-hydroxy-3-methylbenzaldehyde under nitrogen atmosphere. pH of the reaction mass was adjusted to 7.8-8.4 by using NaOH solution. Reaction mass temperature was raised to 40-45° C. Slowly added 48% hydrogen peroxide (2.0 g) and aqueous sodium hydroxide (1.15 g in 30 mL of DM water) to the reaction mass maintaining the pH at 7.8-8.4 and temperature at 40-45° C. Reaction was maintained for 3 h at 45-50° C. for 3 h. Another 2.0 g of 48% hydrogen peroxide and sodium hydroxide (1.15 g in 30 mL DM Water) was added to the reaction mass and maintained for 2 h. The reaction mass was cooled to RT and extracted with ethyl acetate. Organic layer was washed with brine and distilled of solvent to get 3.2 g of crude title compound. The crude compound was purified by column chromatography to get pure compound as syrup. IR (neat): 3395, 2978, 2931, 1604, 1490, 1391, 1314, 1289, 1245, 1201, 1155, 1093, 1055, 984, 882, 841, 797, 730, 688, and 655 cm$^{-1}$. $^1$H-NMR (CDCl$_3$, 400 MHz): δ 6.51-6.61 (m, 2H, ar. H), 5.35 (br. s., exch. with D$_2$O, 1H, OH), 5.17 (s, 2H, OCH$_2$O), 5.01 (br s, 1H, exch. with D$_2$O, OH), 3.76 (q, J=7.2 Hz, 2H, OCH$_2$CH$_3$), 2.16 (s, 3H, ArCH$_3$), 1.25 (t, J=6.8 Hz, 3H, OCH$_2$CH$_3$). $^{13}$C NMR (CDCl$_3$, 100 MHz): δ 149.81 (C-4), 143.14 (C-2), 138.17 (C-1), 115.19 (C-3), 112.01 (C-6), 106.82 (C-5), 94.21 (OCH$_2$O), 64.36 (OCH$_2$CH$_3$), 14.95 (OCH$_2$CH$_3$), 8.76 (ArCH$_3$). Mass (EI-MS): 198.24 (M), 197.10 (M−1).

Example 12

Preparation of ethyl 2-(2,3-dihydroxy-5-(ethoxymethoxy)-4-methylphenyl)-2-hydroxyacetate Into a clean and dry 100 mL flask, were charged 10 mL of THF and 1.0 g of 4-(ethoxymethoxy)-3-methylbenzene-1,2-diol under nitrogen atmosphere. A 3M solution of methylmagnesium chloride in THF (3.6 ml) was slowly added to the reaction mass at 20-25° C. The reaction mass was heated to 40-45° C., maintained for 1 h and distilled of THF under vacuum. Toluene (10 ml) was added to the reaction mass and cooled to 25° C. Ethyl glyoxalate (1.3 g, 50% in toluene) was added to the reaction mass. Temperature was raised to 40-45° C. and maintained for 3 h. Reaction mass was cooled to 15-20° C. and quenched with saturated aqueous ammonium chloride. Reaction mass was extracted with toluene and the combined toluene layer was dried, distilled, the residue purified by column to get the title compound as solid. DSC: 74.17° C. (peak). IR (KBr): 3405, 2980, 2933, 1801, 1739, 1630, 1599, 1502, 1470, 1371, 1300, 1213, 1095, 1061, 1019, 857, 819, and 726 cm$^{-1}$. $^1$H-NMR (CDCl$_3$, 400 MHz): δ 6.54 (s, 1H, Ar. H), 5.26 (s, 1H, CHOH), 5.16 (d, J=3.8 Hz, 2H, OCH$_2$O), 4.21-4.32 (m, 2H, COOCH$_2$CH$_3$), 3.74 (q, J=7.2 Hz, 2H, OCH$_2$CH$_3$), 2.14 (s, 3H, ArCH$_3$), 1.28 (t, J=7.2 Hz, 3H, OCH$_2$CH$_3$), 1.23 (t, J=7.2 Hz, 3H, OCH$_2$CH$_3$). $^{13}$C NMR (CDCl$_3$, 100 MHz): δ 173.21 (CO), 149.68 (C-5), 144.41 (C-3), 136.80 (C-2), 119.75 (C-1), 115.25 (C-4), 105.26 (C-6), 94.09 (OCH$_2$O), 72.10 (CHOH), 64.19 (OCH$_2$CH$_3$), 62.58 (OCH$_2$CH$_3$), 15.02 (OCH$_2$CH$_3$), 13.88 (OCH$_2$CH$_3$), 8.72 (ArCH$_3$). Mass (EI-MS): 300.19 (M), 299.18 (M−1).

Example 13

Preparation of ethyl 2-(6-(ethoxymethoxy)-7-methylbenzo[d][1,3]dioxol-4-yl)-2-hydroxyacetate By following Example 9 procedure, 0.19 g of ethyl 2-(2,3-dihydroxy-5-(ethoxymethoxy)-4-methylphenyl)-2-hydroxyacetate is reacted with 1.0 g of bromochloromethane and 0.65 g of cesium carbonate in DMF medium to get 0.086 g of title compound as syrup. IR (neat): 3481, 2978, 2928, 1739, 1492, 1435, 1397, 1365, 1255, 1209, 1117, 1058, 984, 936, 847, and 718 cm$^{-1}$. $^1$H-NMR (CDCl$_3$, 400 MHz): δ 6.51 (s, 1H, Ar. H), 5.96 (d, J=1.2 Hz, 1H, OCH$_2$O), 5.92 (d, J=1.2 Hz, 1H, OCH$_2$O), 5.17 (br. s., exch. with D$_2$O, 1H, OH), 5.15 (d, J=1.6 Hz, 2H, ArOCH$_2$), 4.19-4.30 (m, 2H, OCH$_2$OCH$_2$CH$_3$), 3.72 (q, J=6.8 Hz, 2H, COOCH$_2$CH$_3$), 2.10 (s, 3H, ArCH$_3$), 1.25 (t, J=7.2 Hz, 3H, OCH$_2$CH$_3$), 1.23 (t, J=7.2 Hz, 3H, OCH$_2$CH$_3$). $^{13}$C NMR (CDCl$_3$, 100 MHz): δ 173.04 (CO), 151.26 (C-6), 146.70 (C-1a), 139.58 (C-3a), 116.38 (C-4), 110.94 (C-7), 105.55 (C-5), 101.30 (C-2), 94.43 (OCH$_2$O), 68.83 (CHOH), 64.29 (OCH$_2$CH$_3$), 62.17 (OCH$_2$CH$_3$), 15.09 (OCH$_2$CH$_3$), 14.04 (OCH$_2$CH$_3$), 8.96 (ArCH$_3$)

We claim:

1. A process for the preparation of 2-substituted-2-(6-(substituted)-7-methylbenzo[d][1,3]dioxol-4-yl)acetic acid derivatives of formula-I,

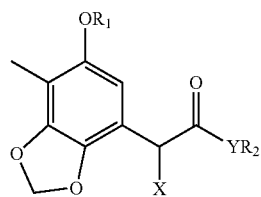

I wherein R$_1$ is a O-protecting group selected from the group consisting of methoxymethyl, ethoxymethyl, trialkylsilyl, arylmethyl, tetrahydropyran-2-yl, and allyl; X is selected from the group consisting of halogen, mesylate, triflate, tosylate, and acetate; Y is selected from the group consisting of an oxygen atom, NH and a sulfur atom; and R$_2$ is C$_1$-C$_6$ alkyl said process comprising:

(i) reacting 2,4-dihydroxy-3-methylbenzaldehyde with an etherification reagent in the presence of a base (or acid in case of tetrahydropyran-2-yl protection) and a solvent at 0-100° C. to produce a mono-protected derivative of formula-XII,

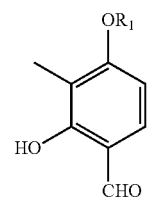

XII wherein R$_1$ is selected from the group consisting of methoxymethyl, ethoxymethyl, trialkylsilyl, tetrahydropyran-2-yl, allyl, and arylmethyl;

(ii) oxidizing said mono-protected derivative of formula-XII with an oxidizing agent in the presence of a base and a solvent at pH 7-14 to obtain a dihydroxy compound of formula-XIII,

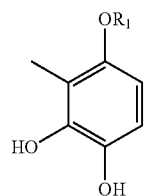

XIII (iii) reacting said dihydroxy compound of formula-XIII with a base and an aldehyde compound of formula-XIV,

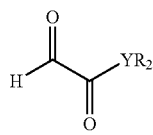

wherein Y and $R_2$ are as defined above;
in the presence of a solvent at 0-100° C. to produce a compound of formula-XV,

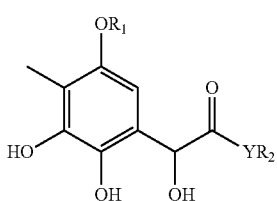

wherein $R_1$, Y, and $R_2$ are as defined above;
(iv) reacting said compound of formula-XV with a dihalomethane in the presence of a base and a solvent at 15-120° C. to produce a methylenedioxy derivative of formula-XVI

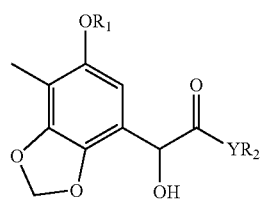

wherein $R_1$, Y, and $R_2$ are as defined above; and
(v) converting the hydroxyl group of said methylenedioxy derivative of formula-XVI to X wherein X is as defined above using a suitable reagent in the presence of a base at −78 to 40° C. to obtain said 2-substituted-2-(6-(substituted)-7-methylbenzo[d][1,3]dioxol-4-yl)acetic acid derivative of formula-I

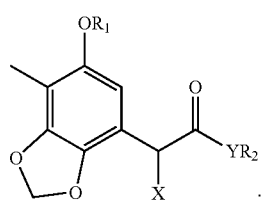

2. A process as claimed in claim 1 wherein the base used in step (i) is selected from the group consisting of trialkylamine, sodium carbonate, potassium carbonate, sodium bicarbonate and potassium bicarbonate.

3. A process as claimed in claim 1 wherein the solvent used in step (i) is selected from the group consisting of halogenated solvents, ethers, and hydrocarbons.

4. A process as claimed in claim 1 wherein the temperature of reaction in step (i) is 10-40° C.

5. A process as claimed in claim 1 wherein the oxidizing agent used in step (ii) is hydrogen peroxide, meta-chloroperbenzoic acid, or peracetic acid.

6. A process as claimed in claim 1 wherein the pH during oxidation in step (ii) is 7.5-8.5.

7. A process as claimed in claim 1 wherein the solvent used in step (ii) is water or aqueous alcohols.

8. A process as claimed in claim 1 wherein the base used in step (ii) is selected from the group consisting of sodium bicarbonate, potassium bicarbonate, sodium carbonate, potassium carbonate and hydroxide.

9. A process as claimed in claim 1 wherein the base used in step (iii) is C1-C6 alkylmagnesium chloride or bromide, or magnesium C1-C6 alkoxide.

10. A process as claimed in claim 1 wherein the temperature of the reaction in step (iii) is 0-45° C.

11. A process as claimed in claim 1 wherein the solvent used in step (iii) is selected from the group consisting of dichloromethane, pentane, hexane, heptane, cyclohexane, toluene, xylene, diethyl ether, tetrahydrofuran (THF), diisopropyl ether, methyl tert-butyl ether, and combinations thereof.

12. A process as claimed in claim 1 wherein the base used in step (iv) is selected from the group consisting of sodium carbonate, potassium carbonate and cesium carbonate.

13. A process as claimed in claim 1 wherein the solvent used in step (iv) is selected from the group consisting of pentane, hexane, heptane, cyclohexane, toluene, xylene, N,N-dimethylformamide, N,N-dimethylacetamide, THF, and acetonitrile.

14. A process as claimed in claim 1 wherein the temperature of the reaction in step (iv) is 25-50° C.

15. A process as claimed in claim 1 wherein the dihalomethane used in step (iv) is bromochloromethane, bromoiodomethane, dibromomethane, dichloromethane, or diiodomethane.

16. A process as claimed in claim 1 wherein the reagent used for conversion of hydroxyl to X in step (v) is thionyl chloride, methanesulfonyl chloride, triflic anhydride, acetyl chloride, acetic anhydride, p-toluenesulfonyl chloride, benzenesulfonyl chloride, carbon tetrachloride/triphenylphosphine, or carbon tetrabromide/triphenylphosphine.

17. A process as claimed in claim 1 wherein the base used for conversion of hydroxyl to X in step (v) is selected from the group consisting of benzotriazole, diazabicycloundecane (DBU), N,N-diisopropylethylamine, and triethylamine.

18. A process as claimed in claim 1 wherein the temperature of the reaction for conversion of hydroxyl to X in step (v) is −40 to 25° C.

19. A compound of formula-XIII,

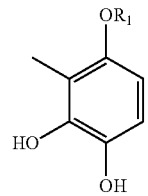

wherein $R_1$ is selected from the group consisting of methoxymethyl, ethoxymethyl, trialkylsilyl, arylmethyl, tetrahydropyran-2-yl, and allyl.

20. A compound of formula XV,

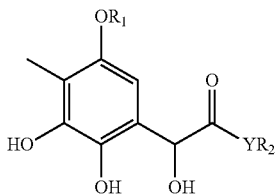

wherein
$R_1$ is selected from the group consisting of methoxymethyl, ethoxymethyl, trialkylsilyl, arylmethyl, tetrahydropyran-2-yl, and allyl;
Y is selected from the group consisting of an oxygen atom, NH and a sulfur atom; and
$R_2$ is $C_1$-$C_6$ alkyl.

21. A process as claimed in claim 2, wherein the trialkylamine is N,N-diisopropylethylamine.

22. A process as claimed in claim 3, wherein the halogenated solvent is methylene chloride.

23. A process as claimed in claim 4, wherein the temperature of reaction in step (i) is 10-25° C.

24. A process as claimed in claim 6, wherein the pH during oxidation in step (ii) is 7.8-8.3.

25. A process as claimed in claim 9, wherein the base used in step (iii) is methylmagnesium chloride or n-butylmagnesium chloride.

26. A process as claimed in claim 11, wherein the solvent in step (iii) is a combination of toluene and THF.

27. A process as claimed in claim 14, wherein the temperature of the reaction in step (iv) is 25-35° C.

* * * * *